United States Patent [19]
Haldenwang

[11] Patent Number: 5,212,083
[45] Date of Patent: May 18, 1993

[54] SEQUENCE FOR STABILIZING PROTEINS IN BACTERIA

[75] Inventor: William G. Haldenwang, San Antonio, Tex.

[73] Assignee: Board of Regents, The University of Texas System, Austin, Tex.

[21] Appl. No.: 736,447

[22] Filed: Jul. 26, 1991

[51] Int. Cl.$^5$ .......................... C12N 9/38; C12N 9/10; C12N 1/00; C07K 15/04

[52] U.S. Cl. .................................... 435/207; 435/193; 435/317.1; 530/300; 530/820; 530/825; 935/44

[58] Field of Search .................. 435/69.1, 69.7, 172.1, 435/172.3, 207; 935/44, 47, 49, 111; 530/324, 300, 820, 825

[56] References Cited

U.S. PATENT DOCUMENTS 5,028,531  7/1991  Ueda .................................. 435/69.4

FOREIGN PATENT DOCUMENTS 0098118  1/1984  European Pat. Off. .
0309237  3/1989  European Pat. Off. .

OTHER PUBLICATIONS

Jonas et al., *J. Bacteriol.*, vol. 172 (1990) 4178–4186, "Phenotypes of *Bacillus subtilis* Mutants Altered in the Precursor-Specific Region of $\sigma^E$".

Bowie and Sauer *The Journal of Biological Chemistry*, 264:13 (1989), 7596–7602, "Identification of C-terminal Extensions That Protect Proteins from Intracellular Proteolysis".

Parsell and Sauer, *The Journal of Biological Chemistry*, 264:13 (1989), pp. 7590–7595, "The Structural Stability of a Protein Is an Important Determinant of Its Proteolytic Susceptibility in *Escherichia coli*".

Héllebust et al., *Journal of Biotechnology*, 12 (1989) 275–284, "Effect of protein fusion on the stability of proteolytically sensitive sites in recombinant DNA proteins".

Sayre et al., *J. Exp. Med.*, 169 (1989) 995–1009, "Structural and Binding Analysis of a Two Domain Extracellular CD2 Molecule".

Spaete et al., *J. Virol.*, 64 (1990) 2922–2931, "Sequence Requirements for Proteolytic Processing of Glycoprotein B of Human Cytomegalovirus Strain Towne".

Dialog Search Report.

Stragier et al. *Nature*, 312 (1984), 376–378, "A developmental gene product of *Bacillus subtilis* homologous to the sigma factor of *Escherichia coli*".

Yanisch-Perron et al., *Gene*, 33 (1985) 103–119, "Improved M13 phage cloning vectors and host strain: nucleotide sequences of the M13mp18 and pUC19 vectors".

Bolivarifi et al., *Gene*, 2 (1977) 95–113, "Construction and Characterization of New Cloning Vehicles; II. A Multipurpose Cloning System".

Adelman et al., *DNA*, 2:3 (1983) 183–193, "In Vitro Deletional Mutagenesis for Bacterial Production of the 20,000-Dalton Form of Human Pituitary Growth Hormone".

Schaeffer et al., *Microbiology*, 54 (1965) 704–711, "Catabolic Repression of Bacterial Sporulation".

(List continued on next page.)

Primary Examiner—Robert A. Wax
Assistant Examiner—Dian Cook
Attorney, Agent, or Firm—Arnold, White & Durkee

[57] ABSTRACT

The invention relates to a protein stabilizing sequence particularly useful for stabilization of proteolytically sensitive proteins. The sequence includes a relatively small number of amino acids that may be expressed fused with a proteolytically sensitive protein. The most effective stabilization sequences assume α-helix structures with a hydrophobic face and a positively charged polar face which appear to require proper orientation with respect to each other. Other aspects of the invention include cloning vectors incorporating a gene sequence encoding the stabilization polypeptide and production of stabilized antigenic proteins.

9 Claims, 3 Drawing Sheets

OTHER PUBLICATIONS

Sanger et al., *Proc. Natl. Acad. Sci.*, 74:12 (1977) 5463–5467, "DNA sequencing with chain-terminating inhibitors".

Kunkel, Proc. Natl. Acad, Sci., 82 (1985) 488–492, "Rapid and efficient site-specific mutageneis without phenotype selection".

Yansura and Henner, *Proc. Natl. Acad. Sci.*, 81 (1984) 439–443, "Use of the *Escherichia coli* lac repressor and operator to control gene expression *Bacillus subtilis*".

Errington, *Journal of General Microbiology* (G.B.), 132 (1986) 2953–2966, "A General Method for Fusion of the *Escherichia coli* lacZ Gene to Chromosomal Genes in *Bacillus subtilis*".

Rong et al., *Journal of Bacteriology*, 165 (1986) 771–779, "Transcriptional Control of the *Bacillus spoIID* Gene".

Gryczan et al., *Journal of Bacteriology*, 134 (1978) 318–329, "Characterization of Staphylococcus aureus Plasmids Introduced by Transformation into *Bacillus subtilis*".

Trempy et al., *Journal of Bacteriology*, 161 (1985) 340–346, "Synthesis of $\sigma^{29}$, an RNA Polymerase Specificity Determinant, Is a Developmentally Regulated Event in *Bacillus subtilis*".

Excerpt by Miller, from Experiments in Molecular Genetics (1972) 351–355, "Assay of $\beta$-Galactosidase".

Hellebust et al., "Different Approaches to Stabilize a Recombinant Fusion Protein," Bio/Technology, 7:165–168, 1989.

Peters et al., "Mutational Analysis of the Precursor-Specific Region of *Bacillus subtilis* $\sigma^E$," J. Bacteriol., 174(14):4629–4637, 1992.

Peters and Haldenwang, "Synthesis and Fractionation Properties of SpoIIGA, a Protein Essential for Pro-$\sigma^E$ Processing in *Bacillus subtilis*," J. Bacteriol., 173(24):7821–7827, 1991.

Stragier et al., "Processing of a Sporulation Sigma Factor in *Bacillus subtilis*: How Morphological Structure Could Control Gene Expression," Cell, 52:697–704, 1988.

```
                                          Pro
                                           ↑
Met  Lys  Lys  Leu  Leu  Arg  Leu  Thr  His  Leu  Trp
 1                                        10   11

Pro
           ↑
Tyr  Lys  Leu  Leu  Met  Lys  Leu  Gly  Leu  Lys  Ser  Asp
               15                        20

Glu  Val  Tyr  Tyr  Ile
                    29
```

FIG. 1

```
ATG  AAA  AAA  CTG  AAA  TTA  CGG  TTG  ACG  CAC  CTC  TGG
 1                                         10

TAT  AAG  CTG  CTG  ATG  AAA  CTT  GGG  CTG  AAA  AGT  GAT
                                    20

GAA  GTC  TAT  TAC  ATA
```

SEQUENCE FOR STABILIZING PROTEINS IN BACTERIA

The United States Government may have certain rights in the present invention pursuant to the terms of Grant No. 86-13978 awarded by the National Science Foundation.

BACKGROUND OF THE INVENTION

1. Field of the Invention

The invention relates to an amino acid sequence useful for stabilization of otherwise unstable proteins, particularly proteolytically sensitive proteins. The invention also relates to methods of producing stabilized proteins by direct attachment of the stabilizing sequence or through fusion proteins expressed from recombinant host cells.

2. Description of Related Art

One of the major problems in the use and preparation of therapeutic and commercial proteins is degradation by cell proteases. This may occur in vivo in plasma or inside a host cell when recombinant methods of polypeptide production are employed. Degradation plays an obvious role in the elimination of damaged or abnormal proteins but also affects half lives of normal proteins. Individual protein turnover rates may vary 1000 fold, depending on environmental and structural factors.

Two general factors contribute to the half-life of any given protein. One factor includes "global" features such as large size, hydrophobicity, thermal instability and charge characteristics. The other factor is related to sequence specific parameters of particular α-amino terminii, asparagine residues and so-called PEST sequences. Although correlations have been made between particular features and susceptibility to degradation, explicit degradation signals and pathways are not well defined. It is not even known whether peptide bond cleavage or biochemical marking is the primary event signaling protein destruction.

In contrast to degradation factors, there appear to be stabilization factors that enhance stability of a protein toward proteolysis. It has been suggested that both thermodynamic stability and proteolytic susceptibility are major determining factors in rate of degradation (Parsell and Sauer, 1989). There has been some evidence that particular sequences at the N-terminus of lambda repressor in *Escherichia coli* aid in maintaining a stable tertiary structure and therefore slow proteolytic degradation (Parsell and Sauer, 1989). Some evidence also suggests that the increased stability of certain fusion proteins may derive from the ability of a stable fusion partner such as protein G or β-galactosidase to stabilize the tertiary structure of a proteolytically sensitive protein (Hèllebust et al., 1989).

A particular amino acid sequence attached as a "tail" to the C-terminal of Arc, a small dimeric DNA-binding protein found in bacteriophage P22, has been found to stabilize that protein against proteolysis. The primary sequence of the tail consists of 25 amino acids which when attached to a heterologous protein, the LP57 mutant of λ-repressor in *Escherichia coli*, also stabilized that protein (Bowie and Sauer, 1989).

Nevertheless, up until now, an amino acid sequence attachable to a proteolytically sensitive protein has not been found which will generally increase stability of these proteins. The value of such a sequence would lie in its ability to increase the half-life of commercially desired proteins for production in recombinant cell hosts and the potential to protect proteinaceous vaccines from serum protease degradation when injected directly into an animal.

SUMMARY OF THE INVENTION

The invention generally relates to a protein stabilization sequence. The sequence is comprised of amino acids that may be attached to proteolytically sensitive proteins.

The stabilization sequence includes a limited number of amino acids ranging from about ten to about 50 residues. The amino acids need not be confined to a particular type of amino acid; however, the amino acid residues will be such that the secondary and tertiary structure assumes the form of an outwardly directed, properly aligned hydrophobic face and a positively charged polar face. The importance of this structure has been shown by substituting two of the amino acids causing the structure to have a twisted form. This form was shown to less stable. The alignment of amino acid groups within a particular α-helical form appears to be important in order for the amino acid sequence to have maximal effect as a stabilization sequence.

The α-helical structure assumed by the amino acid protecting sequence is an important aspect of the invention. Thus it is number and type of amino acid residues involved, and the structure assumed by the amino acid residues making up the structure. Twisted forms of the α-helix structure with the hydrophobic and polar faces out of alignment provide less stability to fused heterologous proteins. Thus in preferred embodiments the outwardly directed hydrophobic face of the structure is in alignment with positively charged face of the α-helix.

Although it is believed that such stabilization structures could be formed with as many as a 100 amino acid residues, the amino acid sequence used is preferably from about 10 to about 50 acid residues and more preferably 29 amino acid residues. A particularly preferred amino acid sequence is shown in FIG. 1(SEQ ID NO: 1).

Another aspect of the invention is the attachment of the protein stabilization sequence to a proteolytically sensitive enzyme. Such attachments may be made at the time of synthesis of the proteolytically sensitive protein of interest or alternatively may be used in in vitro situations where it is desired to protect a proteolytically sensitive protein from degradation. An example might include the use of the protecting sequence to protect an antigenic protein that is being used to promote antibody formation n vivo. Protection of the antigen from serum proteases would provide more effective use of expensive antigenic materials that are in short supply.

In a preferred embodiment, the protein stabilization sequence is prepared in the form of a cassette in which the DNA segment encoding the sequence is incorporated into a cloning vector. Proper construction of the vector results in a protein of interest being expressed with the polypeptide protecting group attached to the protein, thus protecting it from protease degradation within the host cell in which it is expressed.

Attachment of the protein stabilization sequence is generally to the amino-terminal end of the proteolytically sensitive protein or to the carboxy terminal end. In some cases, for example, exceptionally long proteolytically sensitive proteins it may be desirable to attach the stabilization sequence to both termini. In vitro attachment methods may be readily accomplished using chemical attachments well known to those of skill in the art. Attachment of such sequences in vivo is possible by constructing appropriately designed cloning rectors.

The protein stabilization sequence described has general utility and is not limited to stabilization of the polymerase sigma factor from which it was originally derived. RNA polymerase sigma factors from B. subtilis or E. coli have been prepared as fusion proteins with the stabilization factor originally isolated from B. subtilis sigma factor. It is envisioned that virtually any DNA segment encoding a polypeptide could be constructed in a cloning vector or expression vector with the DNA segment encoding the stabilization factor sequence. Examples of other proteolytically sensitive proteins that might be protected with the stabilization sequence include proinsulin, epidermal growth factor, interleukin, interferon, somato tropin, insulin-like growth factor, phosphatase, immunoglobulin Fv and the like. Moreover expression may be from a variety of suitable bacterial cells provided that they can be suitably transformed by an appropriately constructed cloning vector. Examples of suitable host microorganisms include E. coli, B. subtilis, S. tymphyrium and the like.

The invention is also envisioned as a method of enhancing stability of recombinant proteins. A first step would be to obtain a gene segment encoding the protein stabilization sequence. Such a sequence is not limited to a particular number or type of amino acid residues provided that the residues form the appropriate structure having the stabilization properties. Thus under certain conditions it may be desirable to encode up to 100 amino acids in the sequence. In a further step a recombinant vector is prepared. This vector will have a gene encoding the protein stabilization sequence selected as well as a gene encoding a protein desired to be stabilized. Generally, this is accomplished by preparing a cloning site within a plasmid vector that encodes the protein stabilization sequence, then inserting into that site a gene or a gene segment encoding the protein desired to be stabilized. The cloning site may be modified to include one or more unique restriction sites but in general will be constructed so that insertion of the gene of choice will restore a proper reading frame between the protein stabilization sequence and the cloning site through the desired gene segment. Such a recombinant vector may then be used to transform a host cell. Transformed host cell colonies will then be selected, for example by incorporating selected genes within the recombinant vectors su h as antibiotic resistance genes or alkaline phosphatase expressing genes which will elicit positive or negative responses depending on whether the desired gene has been cloned into the cloning site. Once transformed host cell colonies are identified, expression of a heterologous protein fused with the aforedescribed protein stabilization sequence may be affected. This is generally performed using standard culture methods well known to those of skill in the art.

Expression of a wide variety of heterologous proteins fused with the protein stabilization sequences should be possible. In general proteolytically sensitive proteins suitable for production as stable heterologous proteins from prokaryotic hosts will be proteins that are expressible as active fusion proteins. Such proteins include β-galactosidase, sigma factor and the like.

DETAILED DESCRIPTION OF THE PREFERRED EMBODIMENTS

Materials and Methods

Bacterial Strains and Plasmids

B. subtilis strains JH-642 (pheA trpC2) and 1A287 (rpsl) were obtained from J. Hoch and the Bacillus Genetic Stock Center (Ohio State University), respectively. SR104 has an internal deletion in sigE. It was created by transformation of strain SMY with DNA from CM01 (trpC2 pheAl ΔsigE::erm). The M13 host strains CJ236 (dut ung) and JM103 (dut+ ung+) were obtained from V. Deretic (University of Texas Health Science Center at San Antonio). Escherichia coli strain TB-1 was provided by D. Kolodrubetz (University of Texas Health Science Center at San Antonio). Plasmids pSR-5 (spoIID::lacZ) (Rong et al. 1986), pSI-1 (pSpac) (Yansura and Henner, 1984), pGSIIG11 (sigE) (Stragier et al., 1984), and pSGMU31 (Errington, 1986) have been described, pJM102, obtained from J. Hoch, is pUC18 (Yanisch-Perron et al., 1985) with a chloramphenicol acetyltransferase (cat: 950 base pairs [bp]) gene cloned into its unique NdeI site, pSGMU31Δ2 was derived from pSGMU31 by cutting the plasmid at its two BamHI sites and single BglII site and relegating the two major fragments. This results in loss of a small, nonessential BamHI-BglII fragment (150 bp) and the creation of a single BamHI site in the vector. pSGMU31Δ2 has the BamHI site and the lacZ gene of the original plasmid downstream of the plasmid's lac promoter. pSR22 is pBR322 (Bolivar et al., 1977) and pUB11O (Gryczan et al., 1978) joined at their BamHI sites plus a 1.1-kbp fragment encoding sigE (Stragier et al. 1984). The sigE fragment was cloned into the EcoRI site of pBR322 by using EcoRI linkers. pSR51 and pSR54 are variants of pSR22 with missense mutations in the coding sequence of sigE.

Oligonucleotide-Directed Mutagenesis

The 1.1-kpb PstI fragment of pGSIIG11 was cloned into M13mp19 (Yanisch-Perron et al. 1985), and its orientation within the vector was determined by restriction endonuclease analysis of RF DNA. To construct sigEΔ84, an oligonucleotide (60-mer) that carried the sequence 30 bases upstream of and including the ATG codon (nucleotides 179 to 181 of the 1.1-kpb fragment) of $P^{31}$ and 30 bases downstream of the o amino terminus (nucleotides 266 to 268) was synthesized. The 60-mer was hybridized to single-stranded M13 DNA containing its complementary sequence within the cloned 1.1-kpb PstI fragment. The $P^{31}$-specific sequence was "looped out" as a consequence of using DNA polymerase I to synthesize a complement to the circular DNA by using the oligonucleotide as primer. Enrichment for the deleted sequence was accomplished by S1 nuclease treatment of the 84-base loop following the polymerization reaction. The hybridization, polymerization, and S1 treatments were accomplished as described by Adelman et al. (Adelman et al. 1983). Following transformation of *E. coli* JM103, mutagenized clones were screened by restriction endonuclease analysis for reduction in the size of the cloned PstI fragment (i.e., 1.1 kbp to 1.02 kbp) and the loss of the HindII site originally present in the loop region. Approximately 5% of the resulting clones had the desired mutation.

Additional mutant clones sigEΔ81, sigEΔ48, sigEΔ252, and sigEΔ253 were constructed by using oligonucleotides of 30 bases (30-mers) (Kunkel, 1984). M13mp18 containing either the original 1.1-kbp sigE fragment for sigEΔ81 and sigEΔ84) or 1.02-kbp sigEΔ84 fragment (for sigEΔ252 and sigEΔ253) was plaque purified twice on *E. coli* CJ236 (dut ung) and grown on this host to incorporate uracil into the phage DNA. Following hybridization to a 30-mer, Sequenase:2.0 (United States Biochemical Corp., Cleveland, Ohio) was used to synthesize the complementary strand. Selection for the strand polymerized in vitro was accomplished by transforming and plating the polymerization mixture on *E. coli* JM103 (dut+ ung+), which selects against the uracil-containing template. From 50 to 90% of the clones arising from the reaction contained the desired mutations. These were identified by size changes in the cloned *B. subtilis* fragment and by DNA sequencing.

Strain Construction

The *E. coli lac* gene was translationally coupled to sigE by cloning a 340-bp PstI-SauIIIA1 fragment of the 1.1-kbp clones sigE gene into PstI-BamHI-cut pSGMU31Δ2. This coupled the 5' end of IacZ in frame to sigE at a site 165 bp downstream of the sequence encoding the amino terminus of $P^{31}$. In a similar fashion, the 256-bp PstI-SauIII fragment from sigEΔ84 was cloned into this vector. This construct was formed at the same site within sigE but had only 81 bp of the sigE protein-coding region upstream of lacZ. JH642 was transformed with pSGMU31Δ2 containing the coding sequence for either the sigE+− or sigEΔ84-encoded amino terminus. Clones in which the plasmid had integrated into the *B. subtilis* chromosome were selected by chloramphenicol resistance (2.5 μg/ml) and screened by Southern blot analysis for integration into the sigE locus with the proper sigE allele positioned upstream of lacZ.

Strains of JH642 in which the wild-type sigE locus had been replaced by mutant sigE alleles were constructed by congression of the mutant alleles, cloned as a 1- to 1.1-kbp PstI fragment in JM102, with a streptomycin resistance (Str$^r$) marker from *B. subtilis* 1A287. Str$^4$ colonies were screened for Spo$^-$ by failure of the colonies to run brown on DS (Schaeffer et al., 1965) plates after 24 h at 37° C. Spo$^-$ clones were then screened for Cm$^s$ to identify those in which the mutant allele had entered the chromosome by gene replacement rather than integration of the entire plasmid. Chromosomal DNA from clones that met these criteria were screened by Southern blot analysis for the predicted gene replacement.

Analysis of Extracts for $P^{31}$ and $\sigma^E$-like Proteins

*B. subtilis* cultures were grown in DS medium, cells were harvested, and protein extracts were prepared as described previously (Trempy et al., 1985), except that the ammonium sulfate step was omitted. Protein samples (100 μg) (determined by the Coomassie method, Bio-Rad Laboratories) were precipitated with 2 volumes of cold ethanol, suspended in sample buffer, and fractionated on sodium dodecyl sulfate-polyacrylamide gels (12% acrylamide). Following electrophoretic transfer to nitrocellulose and blocking of the nitrocellulose with Blotto, the protein bands were probed with an anti-$P^{31}/\sigma^3$ monoclonal antibody (Trempy et al., 1985). Bound antibody was visualized by using a horseradish peroxidase-conjugated goat immunoglobulin against mouse immunoglobulin (Hyclone Laboratories, Inc.) or $^{125}$I-rabbit anti-mouse immunoglobulin antibody (K. Krolick, University of Texas Health Science Center at San Antonio).

β-Galactosidase Assays

*B. subtilis* strains carrying either pSR5 or an integrated pSGMU31Δ2 plasmid were grown in DS medium and harvested at various times during growth and sporulation. Cells were disrupted by passage through a French pressure Cell (twice at 20,000 lb/in$^2$) and analyzed for B-galactosidase activity as described by Miller (Miller, 1972).

DNA Sequencing

DNA sequencing was performed by the method of Sanger et al. (1977) with the Sequenase reagents (U.S. Biochemical Corp.) and the protocol provided by the manufacturer.

Construction of the sigEΔ84 allele.

The sigE gene was reconfigured to encode a $\sigma^E$-like protein as its direct product. A single-stranded oligonucleotide was hybridized to a region within a single-stranded copy of this fragment (cloned in M13mpl9). This resulted in the looping out of the DNA that encodes the precursor element of $P^{31}$. A complement to the M13-containing DNA was synthesized by using the oligonucleotide as a primer Following second-strand synthesis and destruction of the loop by Sl nuclease, the DNA mixture was introduced into *E. coli* by transformation. Cloned DNAs which both lost the HindII site that is unique to the precursor portion of the sequence and contained a PstI fragment of approximately 1.020 bp (rather than the parental 1.100 bp) were picked as putative sigE mutants (sigEΔ84), expected to contain a sequence in which the region encoding the $\sigma^E$ amino terminus is positioned immediately downstream of the $P^{31}$ initiation codon and ribosome-binding site. This was verified by sequencing the splice regions of constructions that were positive by the restriction endonuclease criteria.

The splice region of one of the clones diverged from the parental sequence only after the initiating ATG codon. At that point, the sequence encoding the $\sigma^E$ amino terminus began in frame with the ATG codon.

The 1.02-kbp PstI fragment carrying the sigEΔ84 allele was cloned into unique PstI sites of the plasmid vectors pJM102 and pSI-1 to form pJMΔ84 and pSIΔ84, respectively. The PstI site of each of these plasmids lay downstream of an IPTG (isopropylthiogalactopyranoside)-inducible promoter) Plac in pJM102 and Pspac in pSI-1). Both plasmids replicated in *E. coli*, but only pSI-1 replicated in *B. subtilis*. The sigEΔ84 gene was cloned in the proper orientation for expression from the inducible promoters as verified by restriction endonuclease analysis of the ability of this gene to specify a product in *E. coli*.

EXAMPLE 1

Production of Sigma Protein in *Escherichia coli*

Figure 3:
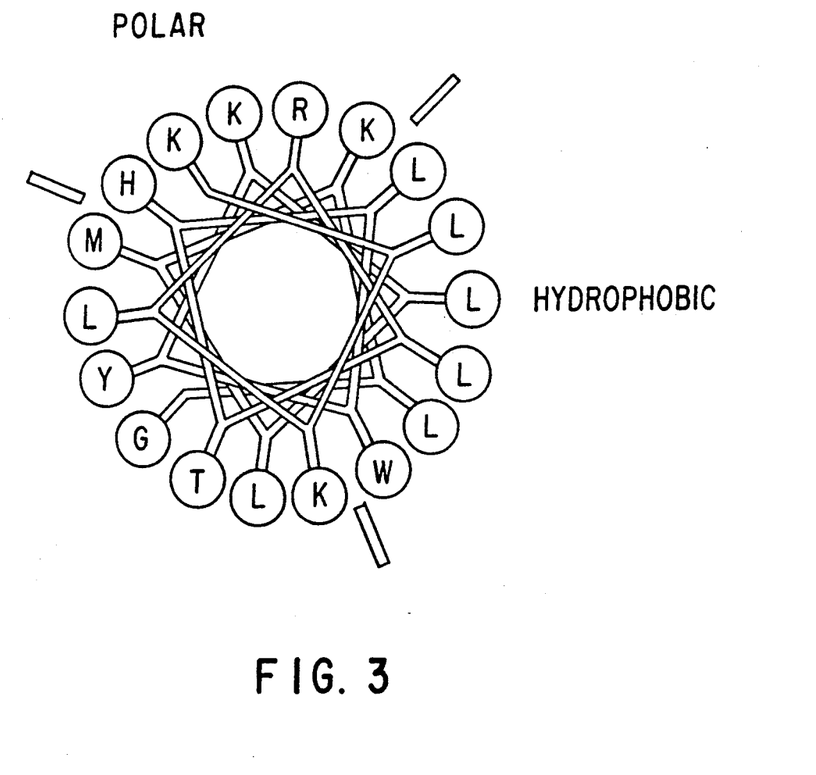
FIG. 3 illustrates generally the α-helix formed by amino acid sequences that confer proteolytic stability on proteins to which they are N-terminally attached. A hydrophobic face and a positively charged polar face are aligned on the α-helix.

Cultures of *E. coli* which carried either the mutant or wild-type sigE allele under Plac or Pspac control were induced with IPTG. The amount of $P^{31}$ or $\sigma^E\Delta 84$ present at 2 h after induction was determined by Western immunoblot analysis. An autoradiogram of the results of this experiment is presented in FIG. 3. Significant amounts of protein that reacted with the anti-$P^{31}/\sigma^E$ antibody were present in all of the extracts. The extracts from strains carrying the sigEΔ84 allele synthesized a protein ($\sigma^E 84$) with the apparent mobility of $\sigma^E$, while the wild-type allele specified a protein with the mobility of $P^{31}$. In addition to the $\sigma^E\Delta 84$ band, extracts prepared from the sigEΔ84 strains contained one or more prominent lower-molecular-weight-proteins that reacted with the antibody. The lower-molecular-weight proteins varied in abundance in different extract preparations and probably represent breakdown products of $\sigma^E$. They were similar in size to but of greater intensity than bands when analyzing extracts of *B. subtilis* cells that synthesize $P^{31}$ and $\sigma^E$ (Jonas et al., 1989). Densitometry measurements of radioactively labeled antibody bound to the Western blots revealed that the amount of the antibody fixed to the two major bands seen in the sigEΔ84 allele encodes a protein with the apparent molecular weight of $\sigma^E$ but the sigEΔ84 product accumulated to a level only 10 to 20% of that obtained from the wild-type sigE allele in *E. coli*.

EXAMPLE 2

Effect of the sigEΔ84 allele on *B. subtilis*

JH642 was transformed with pJMΔ84. Cells that had integrated this nonreplicating plasmid into their chromosomes were selected by chloramphenicol resistance. Recombination between pJMΔ84 and its homologous sequences on the *B. subtilis* chromosome could occur either upstream or downstream of the Δ84 deletion. Recombination upstream of the deletion would place the mutant allele under the control of the spoIIG promoter, allowing it to be expressed. A recombination event downstream of the mutation would leave a wild-type allele as the expressed copy. The Δ84 deletion lay approximately 200 bp from the upstream end of the 1.02-kpb fragment. It was anticipated that approximately 20% of the chloramphenicol-resistant transformants should have the mutant allele as the expressed copy under conditions of random recombination.

Of the 497 transformants receiving pJMΔ84, 127 (25%) were Spo⁻ (i.e., colonies remained white and began to lyse after 24 h at 37° C. on DS medium). In a similar experiment in which the transforming DNA was pJM102 with a wild-type sigE allele (PJME-1), no Spo⁻ transformants were observed (0 of 463). Southern blot analysis of four Spo⁻ and four Spo⁻ clones which had been transformed with pJMΔ84 revealed the wild-type sigE allele as part of the spoIIG operon in the Spo⁺ clones and the sigEΔ84 allele as the operon component in the Spo⁻ clones.

The sigE gene of JH642 was replaced with sigEΔ84 by transforming JH642 (Phe⁻) with SMY chromosomal DNA (Phe⁺) plus plasmid pJMΔ84. Phe⁺ transformants were screened for Spo⁻ clones. The chromosomal DNAs were then examined by Southern blot analysis. These DNAs contained a PstI-generated fragment of 1.03 kbp rather than the parental fragment of 1.1 kpb, which hybridized to a sigE-specific DNA probe. One of these clones (SEΔ84-1) was characterized further.

The activity of the $\sigma^E$ in clone $\sigma^E\Delta 84$-1 was analyzed by using a reporter gene (lacZ) fused to a $\sigma^E$-dependent promoter (spoIID) (Rong et al., 1986). SEΔ84-1 carrying a soIID::acZ fusion made virtually no β-galactosidase during growth or sporulation in DS medium. Western blot analysis failed to detect any $\sigma^E$ at times when $\sigma^E$ is normally abundant. No sigma-type protein was detected in *B. subtilis* when an attempt was made to visualize its product by immunoprecipitation of a radiolabeled product or induction in *B. subtilis* from an spac promoter. Both of these methods generate readily detectable $P^{31}$ and $\sigma^E$ from the wild-type sigE allele.

EXAMPLE 3

Translational Fusions to sigE

A translation fusion between sigE alleles and the *E. coli* lacZ gene was constructed.

As described in the Materials and Methods section, a 340-bp fragment containing upstream DNA and the coding sequence for the first 55 amino acids of $P^{31}$ was cloned into a plasmid vector (pSGMU31Δ2) so as to create an in-frame fusion between $P^{31}$ and the *E. coli* lacZ gene. A similar fusion was created by using the analogous DNA fragment (256 bp) from sigEΔ84. The coding sequence for the first 26 amino acids from the sigEΔ84 gene was fused to lacZ. The vector used was incapable of replication in *B. subtilis* but carried an antibiotic resistance gene (cat) expressible in *B. subtilis*. Thus, transformation of *B. subtilis* with the fusion plasmids followed by selection for chloramphenicol resistance yielded clones in which the plasmid was integrated into its chromosomal homolog. Integration of the plasmid resulted in a Spo⁻ phenotype owing to the positioning of the sigE::lacZ fusion gene within the spoIIG operon in place of the wild-type allele.

When the wild-type sigE::lacZ fusion plasmid was introduced into a sigE⁺ *B. subtilis* strain, all of the clones (38 of 38) displayed a Lac⁺ phenotype on plates (Table 1). In a similar experiment, only 25% (8 of 32) of the transformants receiving the sigEΔ84::lacZ DNA were Lac⁺. As was the case in the previous transformation experiment, the integration event of ::lacZ into sigE could take place either upstream or downstream of the Δ84 mutation. Recombination downstream of the mutation would result in creation of a wild-type sigE::lacZ gene. It was therefore possible that the Lac⁺ clones represented sigE⁺::lacZ fusions and that sigEΔ84::lacZ clones were Lac⁻. A Southern blot analysis of the chromosomes of a representative sample of Lac⁺ and Lac⁻ transformants that had received sigEΔ84::lacZ DNA was performed. Six of six Lac⁺ clones had a DNA fragment of the size anticipated for wild-type sigE upstream of the lacZ gene, and six of six of the Lac⁻ clones had a fragment of the size expected for sigEΔ84 upstream of lacZ.

To verify that a Lac⁻ phenotype is a consequence of the sigEΔ84 sequence being upstream of the lacZ gene the transformation into SE84-1, a strain which already carries the sigEΔ84 allele was repeated. In these experiments, where the creation of a wild-type sigEΔ84 ::lacZ fusion was impossible, all of the chloramphenicol-resistant transformants that received the sigEΔ84 ::lacZ DNA were Lac⁻ (25 or 25), while approximately 15% (4 of 27) of the transformants which received the sigEΔ84 ::lacZ DNA were Lac−. Analysis of the level of B-galactosidase in extracts prepared from sigEΔ84 ::lacZ transformants that were phenotypically Lac− on plates failed to reveal measurable levels of B-galactosidase. Thus, synthesis of the fusion protein mirrors the inability of sigEΔ84 to form $\sigma^E$ itself. In both cases, no product was detectable by the assay systems employed.

TABLE 1

Transformation of *B. subtilis* by sigE::lacZ DNAs[a]

| Recipient | Donor DNA fusion | Total Examined | No. of colonies | | | |
|---|---|---|---|---|---|---|
| | | | Spo+ | Spo− | Lac− | Lac+ |
| JH642 | sigE::lacZ | 38 | 38 | 0 | 38 | 0 |
| | sigEΔ84::lacZ | 32 | 32 | 0 | 8 | 24 |
| SE84 | sigE::lacZ | 27 | 27 | 0 | 23 | 4 |
| | sigEΔ::lacZ | 25 | 25 | 0 | 0 | 25 |

[a]Competent recipient cells were transformed with plasmid DNA. Transformants were selected on LB plates supplemented with chloramphenicol (5 μg ml). Cm' clones were replica plated onto DS plates (22) with and without an agar overlay containing X-gal (5-bromo-4-chloro-3-indolyl-β-/d-thiogalactopyranoside) (0.5 mg/ml) (18). Spo+ colonies turned brown after 24 hr at 37° C. on DS plates, while Spo− colonies remianed white. Lac+ colonies turned blue on DS with X-gal by 18 hr at 37° C.

The cloned sigE gene was mutagenized by using an oligonucleotide (30-mer) that would generate an altered sigEΔ84 with a Lys codon (AAA) between the initiation codon (AUG) and the codon specifying the $\sigma^E$ amino terminus (GGC). Mutant clones were isolated, and their structures were verified by DNA sequencing.

When introduced into *B. subtilis*, sigEΔ81 behaved identically to sigEΔ84. It conferred a Spo− phenotype on cells which carried it (i.e., when sigEΔ84 was cloned into pJM102 and transformed into JH642, approximately 20% of the chloramphenicol-resistant transformants were Spo−), and cells into which the sigEΔ81 allele had been congressed synthesized no detectable $\sigma^E81$ protein. Thus, the addition of AAA at position two of sigEΔ81 yielded no measurable increase in $\sigma^E$ levels.

During the course of the mutagenesis protocol a sigE mutant was generated (sigEΔ48) that encoded a protein with the four amino acids of the amino terminus of sigEΔ81 joined by an Arg residue to residue 22 of P[31]. The sigEΔ48 mutation was initially identified by the intermediate size of the PstI DNA fragment which carried it. Its structure was determined by DNA sequencing.

When sigEΔ48 was moved into *B. subtilis*, the cells became Spo−. However, unlike sigEΔ84 and sigEΔ81, sigEΔ48 synthesized an active $\sigma^E$-like protein. The sigEΔ48 product was seen in Western blots, and its activity was evident by the activation of the spoIID promoter. The activation of the spoIID promoter by sigEΔ48 does not apparently require the processing of $\sigma^E\Delta48$ into the wild-type $\sigma^E$ protein. Transcription of spoIID occurred in *B. subtilis* strains carrying sigEΔ48 even if the strain had a second mutation in a gene (spoIIGA) that is essential for processing. In addition, no change was detected in the mobility of $\sigma^E\Delta48$ at times in sporulation (t4) when the processing activity should be present. Thus, $\sigma^E\Delta48$ is both insensitive to processing and active without processing. The level of product present in the sigEΔ48 strain was comparable to that found in the wild-type sigE strain.

Extracts were produced from *B. subtilis* strains lacking a chromosomal copy of sigE but containing plasmid-borne copies of either the wild-type (sigE+) or one of the mutant alleles of sigE (pSR51 or pSR54). Western blot analysis for proteins of the size of either P[31] or $\sigma^E$-sized proteins in this system indicated no detectable proteins in the extracts prepared from the strains with the mutant sigE alleles. This result was the same obtained with the sigEΔ84 and sigEΔ81 alleles.

EXAMPLE 4

β-qalactosidase Fusion Proteins

*B. subtilis* strains expressing β-galactosidase fusion proteins were constructed as described (Jonas et al., 1990). The *E. coli lacа* gene was translationally coupled to sigE by cloning a 340-bp PstI-auIIIAI fragment of the 1.1 kbp cloned sigE gene into PstI-BamI-cut pSGMU31Δ2. This coupled the 5' end of lacZ in frame to sigE at a site 165 bp downstream of the sequence encoding the amino terminus of P[31]. In a similar fashion, the bp segment encoding the polypeptide having the amino acid sequence of FIG. 1 was cloned into this vector. This construct was formed at the same site within sigE but had only the base pairs shown in FIG. 2 of the sigE protein-coding region upstream of lacZ. JH642 was transformed with pSGMU3Δ12 containing the coding sequence for either the sigE+ or sigEΔ84-encoded amino terminus. Clones in which the plasmid had integrated into the *B. subtilis* chromosome were selected by chloroamphenicol resistance (2.5 μg/ml) and screened by Southern blot analysis for integration into the sigE locus with the proper sigE allele positioned upstream of lacZ.

The half-life of the fusion proteins expressed from transformed *Escherichia coli* or *B. subtilis* host cells were measured. Table 2 shows the results.

TABLE 2

| Protein | Microorganism | Half Life |
|---|---|---|
| Sigma E | *E. coli* | ND |
| β-galactosidase | *E. coli* | 30 min |
| β-galactosidase | *B. subtilis* | ND |
| Sigma E:SS' | *E. coli* | >2 hr |
| β-galactosidase:SS[1] | *E. coli* | |
| β-galactosidase:SS[1] | *B. subtilis* | >2 hr |

Figure 1:
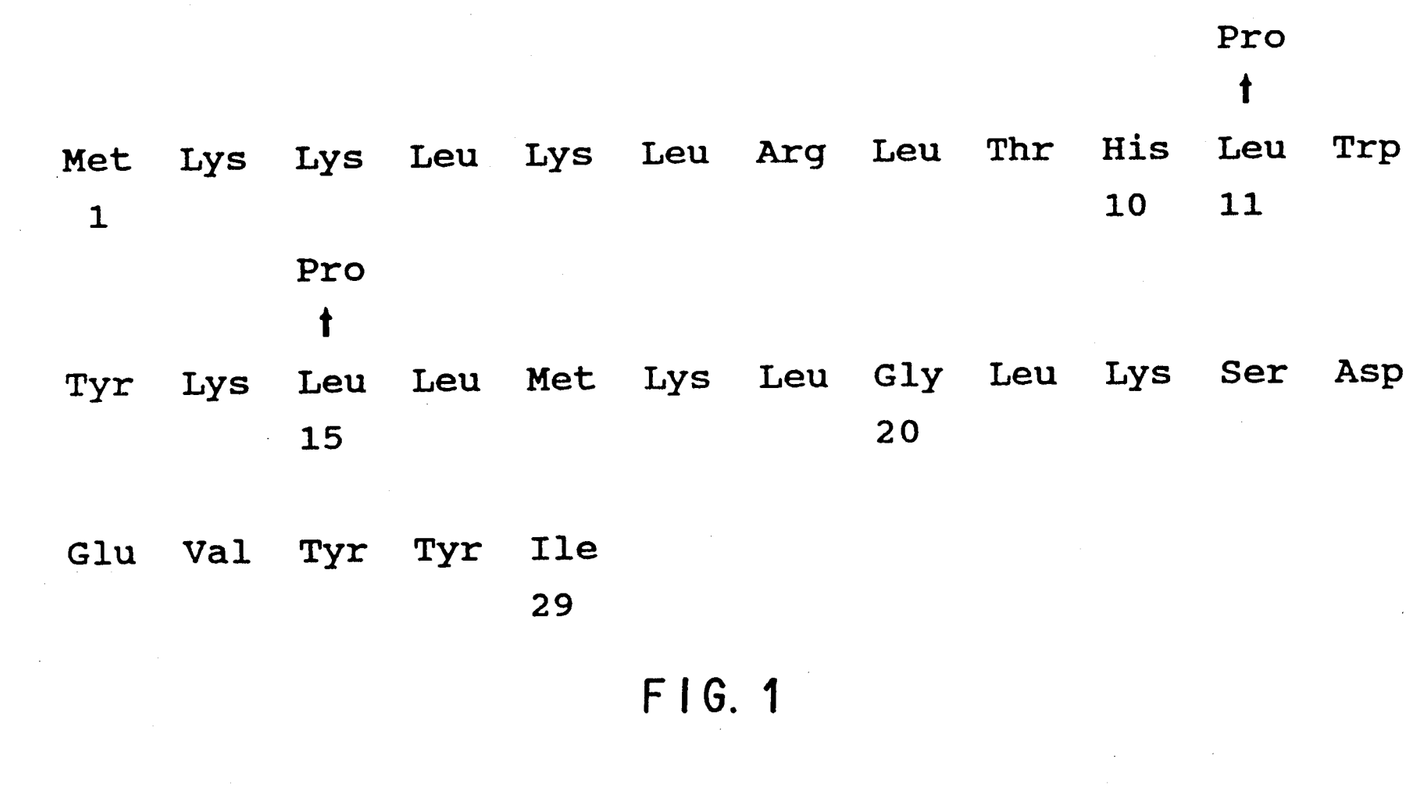
FIG. 1 shows an amino acid sequence (SEQ III NO. 1) capable of forming a protecting hydrophobic faced α-helix structure when attached to a proteolytically sensitive protein.

[1]SS is the 29AA sequence shown in Figure 1.

EXAMPLE 5

Structural Perturbations in Protein Stabilization Sequence

The effect of perturbation of α-helical, structure of the protein stabilization sequence shown in FIG. 1 (SEQ ID NO: 1) was examined by altering the primary amino acid sequence.

Figure 2:
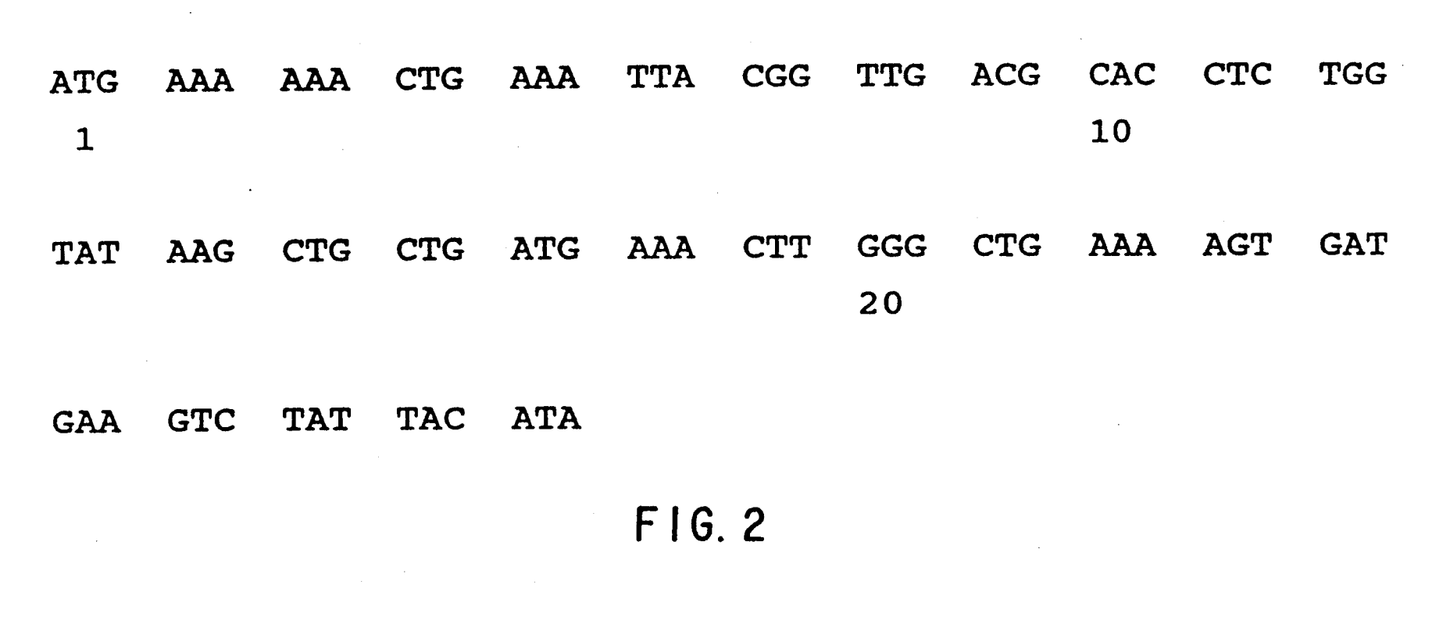
FIG. 2 shows the nucleic acid sequence (SEQ ID NO: 2) which includes encoding a 29 amino acid protective sequence.

The DNA sequence shown in FIG. 2 (SEQ ID NO: 2) was altered by insertion of an arginine codon at position 10, resulting in a new sequence encoding a 30-amino acid polypeptide. In order to effect the insertion, a restriction site was created at codon position 11 by substituting codon CTA for CTC. The base pair segment coding for the 30-amino acid polypeptide and a gene segment encoding β-galactosidase were cloned. Expression of β-galactosidase from a *B. subtilis* bacterial host cell was examined by Western blot. Amounts of expressed fusion polypeptide were less than measured in systems utilizing the 29-amino acid stabilization sequence.

The hydrophobic and hydrophilic faces of the α-helix formed by the 30-amino acid polypeptide were twisted relative to each other by about 100°.

Additional insertions into the DNA sequence encoding the 30 amino acid polypeptide were made. Codons CTC and GCC encoding leucine and alaline were inserted between codon 10 and codon 11 of the base sequence, resulting in a 180° twist of the polypeptide α-helix structure as compared with the α-helix of the 29 amino acid polypeptide structure. The new 32 amino acid polypeptide was expressed as a fusion polypeptide with β-galactosidase from a transformed *B. subtilis* host. Expression was less efficient than with fusions formed from either the 29 or the 30 amino acid protein stabilizing sequence, as indicated by Western blot analysis.

REFERENCES

1. Parsell, D. A. and Sauer, R. T., *J. Biol. Chem.* 264. 7590-7995 (1989).
2. Hellenbust, H., Uhlen, M. and Enfors, S. -O., *J. Biotechnology* 12, 175-284 (1989).
3. Bowie, J. U. and Sauer, R. T., *J. Biol. Chem.* 264, 7597-7602 (1989).
4. Rong, S., Rosenkrantz, M. S. and Sonenshein, A. L., *J. Bacteriol.* 165:771-779 (1986).
5. Yansura, D. G. and Henner, D. J., *Proc. Natl. Acad. Sci. U.S.A.* 81:439-443 (1984).
6. Stragier, P., Bouvier, J., Bonamy, C. and Szulmajster, J., *Nature* 312:376-378 (1984).
7. Errington, J., *J. Gen. Microbiol.*, 132:2953-2966 (1986).
8. Yanisch-Perron, C., Vieira, J. and Messing, J., *Gene* 33:103-119 (1985).
9. bolivar, F., Rodriguez, r. L., Greene, P. J., Betlach, M. C., Heynecker, H. L., Boyer, H. W., Crosa, J. H. and Falkow, S., *Gene* 2:95-113 (1977).
10. Gryczan, T. J., Contente, S. and Dubnau, D., *J. Bacteriol.* 134:318-329 (1978).
11. Adelman, J. P., Hayflick, J. S., Vasser, M. and Seeburg, P. H., *DNA b 2:183-193* (1983).
12. Kunkel, T. A., *Proc. Natl. Acad. Sci. U.S.A.* 82:488-492 (1984).
13. Schaeffer, P., Millet, J. and Aubert, J., *Proc. Natl. Acad. Sci. U.S.A.* 54:704-711 (1965).
14. Trempy, J. E., Morrison-Plummer, J. and Haldenwang, W. G., *J. Bacteriol.* 161:340-346 (1965).
15. Miller, J. H., Experiments in molecular genetics, Cold Spring Harbor Laboratory, Cold Spring Harbor, New York (1972).
16. Sanger, F., Nicklen, S. and Coulson, A. R., *Proc. Natl. Acad. Sci. U.S.A.* 74:5463-5467 (1977).
17. Jonas, R. M. and Haldenwang, W. G., *J. Bacteriol.* 171:5226-5228 (1989).

---

I claim:

1. An isolated and purified peptide consisting essentially of about 29–31 amino acids contained in an inactive precursor protein of sporulation specific *Bacillus subtilis* factor, wherein said peptide is capable of enhancing protein stability when attached to a protein sensitive to degradation.

2. The peptide of claim 1 wherein the amino acid residues are capable of forming a structure having an outwardly directed hydrophobic face and a positively charged polar face.

3. The peptide of claim 2 wherein the outwardly directed hydrophobic face is in alignment with the positively charged polar face.

4. The peptide of claim 3 having an alpha helix structure.

5. The isolated and purified peptide of claim 1 which has an amino acid sequence in accordance with SEQ ID NO: 1.

6. An isolated and purified peptide consisting essentially of 30 amino acid residues in accordance with SEQ ID NO:1 wherein arginine is inserted at position 10 between the his and leu residues.

7. An isolated and purified peptide consisting essentially of 32 amino acid residues in accordance with SEQ ID NO: 1 by insertion of arginine, leucine and alanine between the amino acid residues at positions 10 and 11.

8. A method of stabilizing RNA polymerase sigma factor, RNA polymerase sigma-like factor, β-galactosidase or β-galactosidase-like polypeptides comprising attaching the peptide sequence of any of claims 1, 6 or 7 to the amino terminal end of the polypeptide or protein.

9. The method of claim 8 wherein the RNA polymerase sigma factor is from *Bacillus subtilis* or *Escherichia coli*.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) TOPOLOGY: linear     ( i i ) MOLECULE TYPE: peptide     ( x i ) SEQUENCE DESCRIPTION: SEQ ID NO:1:

```
Met Lys Lys Leu Lys Leu Arg Leu Thr His Leu Trp Tyr Lys Leu Leu
1               5                   10                  15
Met Lys Leu Gly Leu Lys Ser Asp Glu Val Tyr Tyr Ile
                20                  25
```

( 2 ) INFORMATION FOR SEQ ID NO:2:

( i ) SEQUENCE CHARACTERISTICS:
        ( A ) LENGTH: 171 base pairs
        ( B ) TYPE: nucleic acid
        ( C ) STRANDEDNESS: unknown
        ( D ) TOPOLOGY: linear     ( i i ) MOLECULE TYPE: oligonucleotide     ( x i ) SEQUENCE DESCRIPTION: SEQ ID NO:2:

```
ATG AAA AAA CTG AAA TTA CGG TTG ACG CAC CTC TGG TAT AAG CTG          45
Met Lys Lys Leu Lys Leu Arg Leu Thr His Leu Trp Tyr Lys Leu
                5                   10                  15

CTG ATG AAA CTT GGG CTG AAA AGT GAT GAA GTC TAT TAC ATA GGC          90
Leu Met Lys Leu Gly Leu Lys Ser Asp Glu Val Tyr Tyr Ile Gly
                20                  25                  30

GGG AGT GAA GCC CTG CCG CCT CCA TTA TCT AAA GAT GAG GAG CAG         135
Gly Ser Glu Ala Leu Pro Pro Pro Leu Ser Lys Asp Glu Glu Gln
                35                  40                  45
```

```
GTT TTG TTA ATG AAG CTC CCA AAC GGC GAT CAG GCG                171
Val Leu Leu Met Lys Leu Pro Asn Gly Asp Gln Ala
            50                      55
```